United States Patent [19]

Butler et al.

[11] Patent Number: 4,584,313

[45] Date of Patent: Apr. 22, 1986

[54] (SUBSTITUTED-PHENYL)-5-OXO-2-PYR-ROLIDINEPROPANOIC ACIDS AND ESTERS THEREOF, AND USE FOR REVERSING ELECTROCONVULSIVE SHOCK-INDUCED AMNESIA

[75] Inventors: Donald E. Butler; Anthony J. Thomas, both of Ann Arbor, Mich.

[73] Assignee: Warner-Lambert Company, Morris Plains, N.J.

[21] Appl. No.: 607,376

[22] Filed: May 7, 1984

[51] Int. Cl.$^4$ .................... C07D 207/36; A61K 31/40
[52] U.S. Cl. ..................................... 514/424; 548/543
[58] Field of Search ......................... 548/543; 514/424

[56] References Cited

U.S. PATENT DOCUMENTS 4,012,495  3/1977  Schmiechen et al. ............. 548/543
4,198,514  4/1980  Imanishi et al. .................... 548/543

Primary Examiner—Glennon H. Hollrah
Assistant Examiner—David B. Springer
Attorney, Agent, or Firm—Jerry F. Janssen

[57] ABSTRACT

Certain 5-oxo-3-(unsubstituted-phenyl)- or 5-oxo-3-(substituted phenyl)-2-pyrrolidinepropanoic acids and 5-oxo-$\beta$-(unsubstituted-phenyl)- or 5-oxo-$\beta$-(substituted-phenyl)-2-pyrrolidinepropanoic acids, their pharmaceutically acceptable esters and metal and amine cation salts, pharmaceutical compositions employing these compounds, and a method of treating senility or of reversing amnesia are disclosed.

19 Claims, No Drawings

(SUBSTITUTED-PHENYL)-5-OXO-2-PYRROLIDINEPROPANOIC ACIDS AND ESTERS THEREOF, AND USE FOR REVERSING ELECTROCONVULSIVE SHOCK-INDUCED AMNESIA

BACKGROUND OF THE INVENTION

The present invention relates to compounds, pharmaceutical compositions based thereon, and a method of treating senility or of reversing amnesia. More particularly, it is concerned with certain related 5-oxo-3-(unsubstituted-phenyl)- or 5-oxo-3-(substituted-phenyl)-2-pyrrolidinepropanoic acids and 5-oxo-β-(unsubstituted-phenyl)- or 5-oxo-β-(substituted-phenyl)-2-pyrrolidinepropanoic acids, their pharmaceutically acceptable esters and metal and amine cation salts, pharmaceutical compositions employing these compounds, and a method of treating senility or of reversing amnesia.

SUMMARY AND DETAILED DESCRIPTION

In its broadest aspect, the present invention relates to compounds having structural formula I or II:

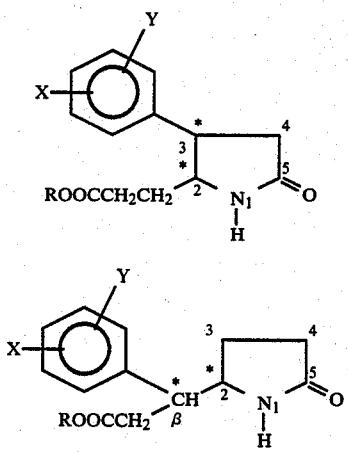

wherein R is hydrogen, a pharmaceutically acceptable metal or amine cation, alkyl of from one to six carbon atoms, phenyl, or phenylmethyl, and X and Y are independently hydrogen, alkyl of from one to six carbon atoms, alkoxy of from one to six carbon atoms, chloro- or trifluoromethyl.

Compounds of structural formulae I and II above form a class of closely interrelated compounds. The same reaction sequence is used to prepare compounds of both generic formulae I and II, and the compounds are directly interconvertible through a common bicyclic intermediate, as detailed further below.

The reactions leading to the compounds of the present invention result in the production of molecules in which there are two asymmetric centers. In the substituted 5-oxo-2-pyrrolidinepropanoic acids of formula I, an asymmetric center exists at positions 2 and 3 on the pyrrolidine ring, whereas, in 5-oxo-2-pyrrolidinepropanoic acids of formula II, an asymmetric center exists at position 2 on the pyrrolidine ring and at the β carbon atom of the propanoic acid side chain. These asymmetric centers have been indicated in the structural formulas given above by asterisks.

In addition, the 5-oxo-2-pyrrolidinepropanoic acids of formula I are capable of existing as geometric isomers in which the phenyl substituent group at position 3 of the pyrrolidine ring and the propanoic acid side chain at position 2 may be in either a cis- or transconfiguration with respect to one another.

The present invention contemplates all possible stereoisomers and geometric isomers of the compounds represented by structural formulae I and II, as well as mixtures thereof.

The terms "geometric isomers," "enantiomeric forms," and "stereoisomers" are those understood by practitioners of the organic chemical art, more specifically, as defined by E. L. Eliel, "Stereochemistry of Carbon Compounds," McGraw-Hill, New York, 1962.

By the term "alkyl of from one to six carbon atoms" is meant any branched or unbranched saturated hydrocarbon grouping containing from one to six carbon atoms. Such groups include, by way of example, methyl, ethyl, n-propyl, iso-propyl, n-, sec-, iso-, and tert-butyl, n-, sec-, iso-, and neo-pentyl, n-hexyl, and the like.

By the term "alkoxy of from one to six carbon atoms: is meant any moiety containing an alkyl group as defined above, attached through an oxygen atom to the parent molecular subunit.

The acidic compounds of the present invention form salts with pharmaceutically acceptable metal or amine cations derived from organic and inorganic bases. The term "pharmaceutically acceptable metal cation" contemplates positively charged metal ions such as those derived from sodium, potassium, calcium, magnesium, aluminum, iron, zinc, and the like.

The term "pharmaceutically acceptable amine cation" contemplates the positively charged ions derived from ammonia and organic nitrogenous bases strong enough to form such cations. Bases useful for the formation of pharmaceutically acceptable non-toxic acid addition salts of compounds containing a carboxyl acid function form a class whose limits are readily understood by those skilled in the art.

Merely for illustration, this class of amines can be said to comprise, in cationic form, those of the formula:

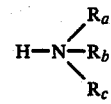

wherein $R_a$, $R_b$, and $R_c$ independently are hydrogen, alkyl of from one to six carbon atoms, cycloalkyl of from about three to six carbon atoms, aryl, aralkyl of from about seven to about ten carbon atoms, hydroxyalkyl of from two to four carbon atoms, or monoarylhydroxyalkyl of from about eight to about fifteen carbon atoms. Further, when taken together with the nitrogen atom to which they are attached, any two of $R_a$, $R_b$, and $R_c$ may form part of a five-or six-membered nitrogen-containing heterocyclic aromatic or non-aromatic ring containing carbon or oxygen, said nitrogen-containing heterocyclic rings being unsubstituted, monosubstituted, or disubstituted with alkyl groups of from one to six carbon atoms.

Specific examples of organic amine cations contemplated as falling within the scope of the present invention include mono-, di-, and trimethylammonium, mono-, di-, and triethylammonium, mono-, di-, and tripropylammonium (n-propyl and isopropyl), ethyldimethylammonium, benzylammonium, dibenzylammonium, benzyldimethylammonium, cyclohexylammonium, piperidinium, morpholinium, pyrrolidinium, 4-ethylmorpholinium, 1-isopropylpyrrolidinium, 1,4-dimethylpiperazinium, 1-n-butylpiperidinium, 2-methylpiperidinium, 1-ethyl-2-methylpiperidinium, mono-, di-, and triethanolammonium, ethyldiethanolammonium, n-butylmonoethanolammonium, tris(hydroxymethyl)methylammonium, phenylmonoethanolammonium, and the like.

The ammonium, amine, or metal salts are prepared by reaction of the appropriate acetic or propanoic acid compound of this invention with an equivalent amount of an organic amine base or an inorganic base such as ammonium hydroxide, sodium hydroxide, potassium hydroxide, sodium carbonate, calcium carbonate, sodium bicarbonate, and the like in an appropriate solvent such as water or an aqueous alcohol, followed by removal of the solvent under reduced pressure.

The free acid form of the compound may be regenerated from the salts, if desired, by contacting the salt with a dilute aqueous solution of an acid such as hydrochloric.

The compounds of the present invention may also exist in the solvated form in which the compound is solvated with water, lower alcohols such as ethanol, propanol and the like, or other pharmaceutically acceptable solvents employed in the synthesis of the materials. Although the solvated and unsolvated forms of the compounds may differ somewhat in their physical properties such as melting point and solubility, they are considered equivalent for the purposes of the invention.

Representative examples of compounds contemplated as falling within the scope of the present invention include the following:

5-Oxo-3-phenyl-2-pyrrolidinepropanoic acid and the pharmaceutically acceptable metal and amine cation salts thereof;
5-Oxo-3-phenyl-2-pyrrolidinepropanoic acid methyl ester;
5-Oxo-3-phenyl-2-pyrrolidinepropanoic acid ethyl ester;
5-Oxo-3-phenyl-2-pyrrolidinepropanoic acid 1,1-dimethylethyl ester;
5-Oxo-3-phenyl-2-pyrrolidinepropanoic acid phenyl ester;
5-Oxo-3-phenyl-2-pyrrolidinepropanoic acid phenylmethyl ester;
5-Oxo-β-phenyl-2-pyrrolidinepropanoic acid and the pharmaceutically acceptable metal and amine cation salts thereof;
5-Oxo-β-phenyl-2-pyrrolidinepropanoic acid methyl ester;
5-Oxo-β-phenyl-2-pyrrolidinepropanoic acid ethyl ester;
5-Oxo-β-phenyl-2-pyrrolidinepropanoic acid 1,1-dimethylethyl ester;
5-Oxo-β-phenyl-2-pyrrolidinepropanoic acid phenyl ester;
5-Oxo-β-phenyl-2-pyrrolidinepropanoic acid phenylmethyl ester;
3-(4-Methylphenyl)-5-oxo-2-pyrrolidinepropanoic acid and the pharmaceutically acceptable metal and amine cation salts thereof;
3-(4-Methylphenyl)-5-oxo-2-pyrrolidinepropanoic acid methyl ester;
3-(4-Methylphenyl)-5-oxo-2-pyrrolidinepropanoic acid ethyl ester;
3-(4-Methylphenyl)-5-oxo-2-pyrrolidinepropanoic acid 1,1-dimethylethyl ester;
3-(4-Methylphenyl)-5-oxo-2-pyrrolidinepropanoic acid phenyl ester;
3-(4-Methylphenyl)-5-oxo-2-pyrrolidinepropanoic acid phenylmethyl ester;
β-(4-Methylphenyl)-5-oxo-2-pyrrolidinepropanoic acid and the pharmaceutically acceptable metal and amine cation salts thereof;
β-(4-Methylphenyl)-5-oxo-2-pyrrolidinepropanoic acid methyl ester;
β-(4-Methylphenyl)-5-oxo-2-pyrrolidinepropanoic acid ethyl ester;
β-(4-Methylphenyl)-5-oxo-2-pyrrolidinepropanoic acid 1,1-dimethylethyl ester;
β-(4-Methylphenyl)-5-oxo-2-pyrrolidinepropanoic acid phenyl ester; and
β-(4-Methylphenyl)-5-oxo-2-pyrrolidinepropanoic acid phenylmethyl ester.
3-(4-Chlorophenyl)-5-oxo-2-pyrrolidinepropanoic acid and the pharmaceutically acceptable metal and amine cation salts thereof;
3-(4-Chlorophenyl)-5-oxo-2-pyrrolidinepropanoic acid methyl ester;
3-(4-Chlorophenyl)-5-oxo-2-pyrrolidinepropanoic acid ethyl ester;
3-(4-Chlorophenyl)-5-oxo-2-pyrrolidinepropanoic acid 1,1-dimethylethyl ester;
3-(4-Chlorophenyl)-5-oxo-2-pyrrolidinepropanoic acid phenyl ester;
3-(4-Chlorophenyl)-5-oxo-2-pyrrolidinepropanoic acid phenylmethyl ester;
β-(4-Chlorophenyl)-5-oxo-2-pyrrolidinepropanoic acid and the pharmaceutically acceptable metal and amine cation salts thereof;
β-(4-Chlorophenyl)-5-oxo-2-pyrrolidinepropanoic acid methyl ester;
β-(4-Chlorophenyl)-5-oxo-2-pyrrolidinepropenoic acid ethyl ester;
β-(4-Chlorophenyl)-5-oxo-2-pyrrolidinepropanoic acid 1,1-dimethylethyl ester;
β-(4-Chlorophenyl)-5-oxo-2-pyrrolidinepropanoic acid phenyl ester;
β-(4-Chlorophenyl)-5-oxo-2-pyrrolidinepropanoic acid phenylmethyl ester;
3-(3,4-Dichlorophenyl)-5-oxo-2-pyrrolidinepropanoic acid and the pharmaceutically acceptable metal and amine cation salts thereof;
3-(3,4-Dichlorophenyl)-5-oxo-2-pyrrolidinepropanoic acid methyl ester;
3-(3,4-Dichlorophenyl)-5-oxo-2-pyrrolidinepropanoic acid ethyl ester;
3-(3,4-Dichlorophenyl)-5-oxo-2-pyrrolidinepropanoic acid 1,1-dimethylethyl ester;
3-(3,4-Dichlorophenyl)-5-oxo-2-pyrrolidinepropanoic acid phenyl ester;
3-(3,4-Dichlorophenyl)-5-oxo-2-pyrrolidinepropanoic acid phenylmethyl ester;
β-(3,4-Dichlorophenyl)-5-oxo-2-pyrrolidinepropanoic acid and the pharmaceutically acceptable metal and amine cation salts thereof;
β-(3,4-Dichlorophenyl)-5-oxo-2-pyrrolidinepropanoic acid methyl ester;
β-(3,4-Dichlorophenyl)-5-oxo-2-pyrrolidinepropanoic acid ethyl ester;
β-(3,4-Dichlorophenyl)-5-oxo-2-pyrrolidinepropanoic acid 1,1-dimethylethyl ester;
β-(3,4-Dichlorophenyl)-5-oxo-2-pyrrolidinepropanoic acid phenyl ester;

β-(3,4-Dichlorophenyl)-5-oxo-2-pyrrolidinepropanoic acid phenylmethyl ester;

5-Oxo-3-[4-(trifluoromethyl)phenyl]-2-pyrrolidinepropanoic acid and the pharmaceutically acceptable metal and amine cation salts thereof;

5-Oxo-3-[4-(trifluoromethyl)phenyl]-2-pyrrolidinepropanoic acid methyl ester;

5-Oxo-3-[4-(trifluoromethyl)phenyl]-2-pyrrolidinepropanoic acid ethyl ester;

5-Oxo-3-[4-(trifluoromethyl)phenyl]-2-pyrrolidinepropanoic acid 1,1-dimethylethyl ester;

5-Oxo-3-[4-(trifluoromethyl)phenyl]-2-pyrrolidinepropanoic acid phenyl ester;

5-Oxo-3-[4-(trifluoromethyl)phenyl]-2-pyrrolidinepropanoic acid phenylmethyl ester;

5-Oxo-β-[4-(trifluoromethyl)phenyl]-2-pyrrolidinepropanoic acid and the pharmaceutically acceptable metal and amine cation salts thereof;

5-Oxo-β-[4-(trifluoromethyl)phenyl]-2-pyrrolidinepropanoic acid methyl ester;

5-Oxo-β-[4-(trifluoromethyl)phenyl]-2-pyrrolidinepropanoic acid ethyl ester;

5-Oxo-β-[4-(trifluoromethyl)phenyl]-2-pyrrolidinepropanoic acid 1,1-dimethylethyl ester;

5-Oxo-β-[4-(trifluoromethyl)phenyl]-2-pyrrolidinepropanoic acid phenyl ester;

5-Oxo-β-[4-(trifluoromethyl)phenyl]-2-pyrrolidinepropanoic acid phenylmethyl ester;

3-(4-Methoxyphenyl)-5-oxo-2-pyrrolidinepropanoic acid and the pharmaceutically acceptable metal and amine cation salts thereof;

3-(4-Methoxyphenyl)-5-oxo-2-pyrrolidinepropanoic acid methyl ester;

3-(4-Methoxyphenyl)-5-oxo-2-pyrrolidinepropanoic acid ethyl ester;

3-(4-Methoxyphenyl)-5-oxo-2-pyrrolidinepropanoic acid 1,1-dimethylethyl ester;

3-(4-Methoxyphenyl)-5-oxo-2-pyrrolidinepropanoic acid phenyl ester;

3-(4-Methoxyphenyl)-5-oxo-2-pyrrolidinepropanoic acid phenylmethyl ester;

β-(4-Methoxyphenyl)-5-oxo-2-pyrrolidinepropanoic acid and the pharmaceutically acceptable metal and amine cation salts thereof;

β-(4-Methoxyphenyl)-5-oxo-2-pyrrolidinepropanoic acid methyl ester;

β-(4-Methoxyphenyl)-5-oxo-2-pyrrolidinepropanoic acid ethyl ester;

β-(4-Methoxyphenyl)-5-oxo-2-pyrrolidinepropanoic acid 1,1-dimethylethyl ester;

β-(4-Methoxyphenyl)-5-oxo-2-pyrrolidinepropanoic acid phenyl ester; and

β-(4-Methoxyphenyl)-5-oxo-2-pyrrolidinepropanoic acid phenylmethyl ester.

Compounds of the present invention, corresponding to structural formulae I and II, above, are prepared by cyclizing a compound having the general formula VIII, wherein X and Y have the values defined above, and $R_1$ and $R_2$ may be the same or different and are selected from methyl, ethyl, 1,1-dimethylethyl, phenyl, or phenylmethyl.

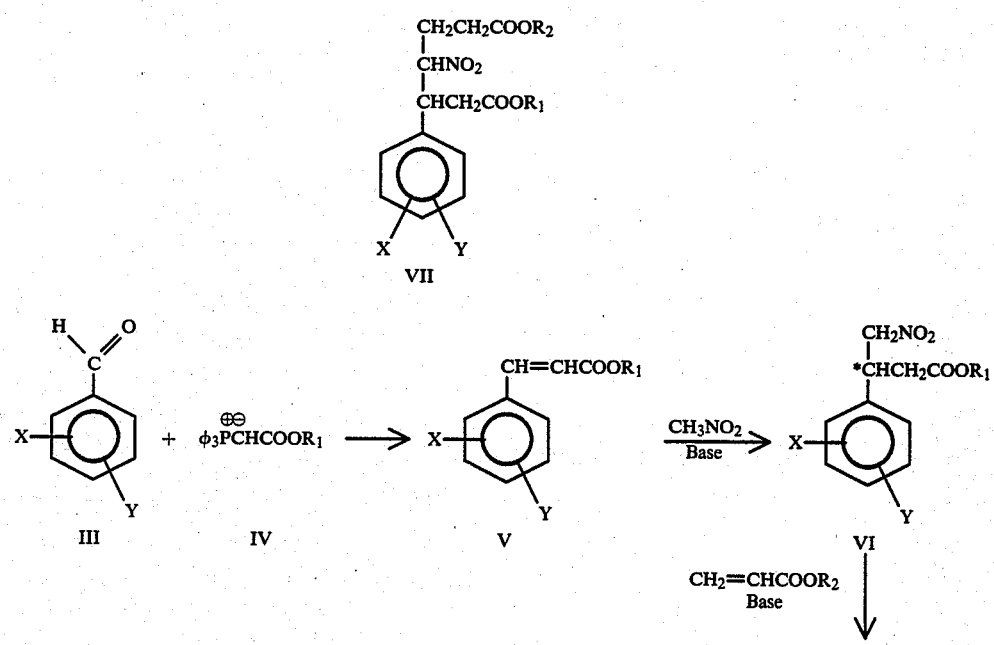

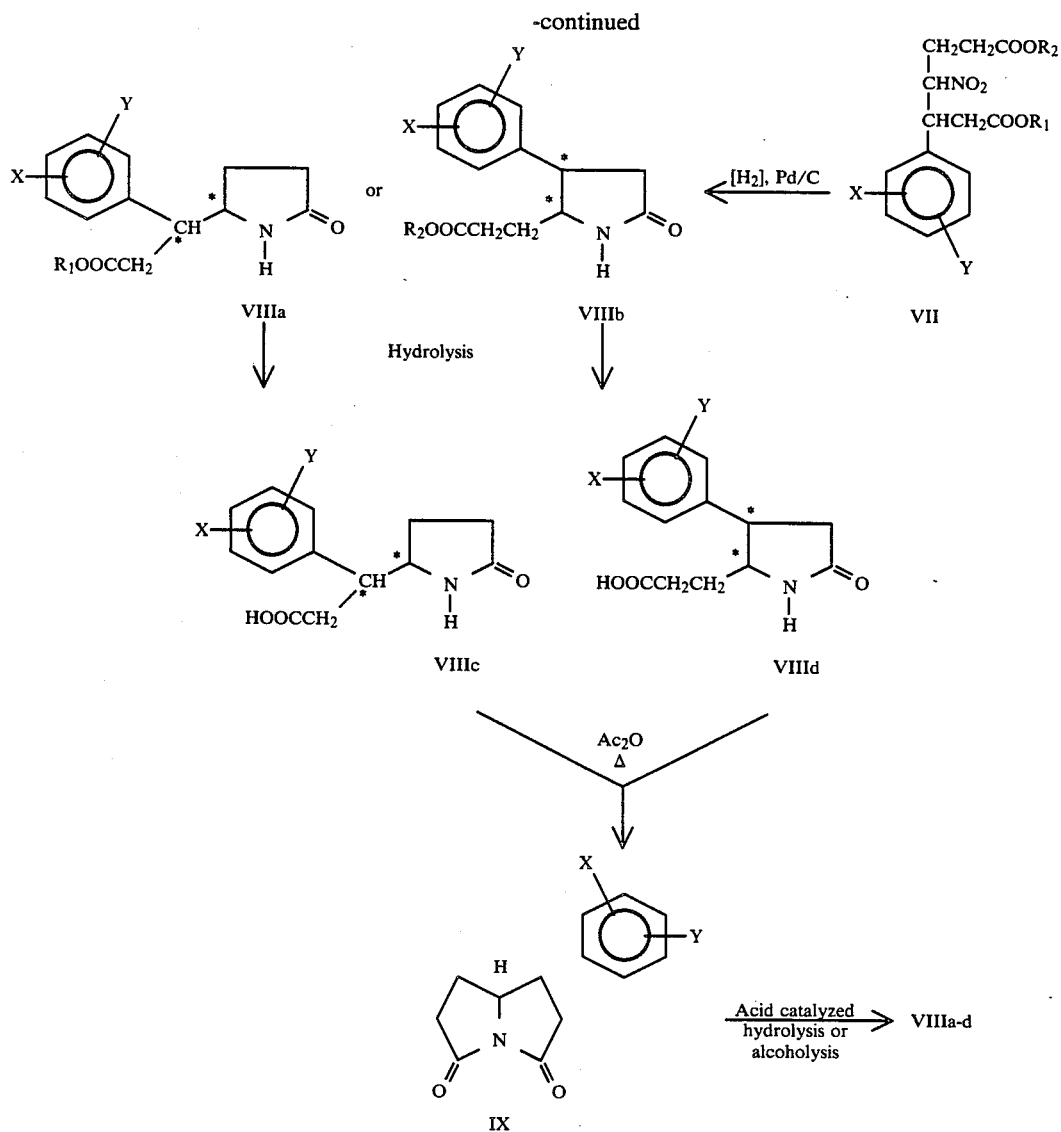

The known mono- or disubstituted benzaldehydes, III, are reacted with the phosphorus ylid IV to yield the substituted cinnamic acid esters, V many of which are known compounds, in the well-known Wittig Reaction (cf U. Schöllkopf, Ang. Chem., 71:260 (1959)).

If the desired end products of the sequence are the mixtures of esters VIIIa and VIIIb, or the mixtures of the corresponding acids, VIIIc and VIIId, the methyl, ethyl, or phenyl ester of the phosporus ylid, IV, is employed in the first step of the sequence (i.e. $R_1$=methyl, ethyl, or phenyl). The resulting substituted or unsubstituted cinnamic acid esters, V, are reacted with nitromethane in the presence of base to produce the nitroesters, VI. Condensation of the nitro-esters, VI, with an acrylate ester in the presence of a base yields the corresponding substitute nitro-heptanedioic acid esters, VII.

In the next step of the reaction sequence, the nitroheptane-dioic acid esters, VII, are reacted with hydrogen in the presence of a catalyst such as Pd/C to simultaneously reduce the nitro-group and, under these conditions, form the 5-oxo-pyrrolidine-ring to yield the mixture of esters, VIIIa and VIIIb.

The mixture of acids, VIIIc and VIIId, if desired, is obtained from the mixture of esters, VIIIa and VIIIb, by simple hydrolysis with dilute aqueous base, followed by acidification.

If the desired end products of the reaction sequence are exclusively the substituted 5-oxo-2-pyrrolidine-propanoic esters, VIIIa, or the corresponding acids, VIIIc, the 1,1-dimethylethyl ester of the phosphorus ylid, IV, is employed in the first step of the reaction scheme (i.e., $R_1$=1,1-dimethylethyl). Alternatively, the nitro-butyric acid ester, VI, may be converted from a simple ester such as the methyl or ethyl ester, to the 1,1-dimethylethyl ester, when desired, by conventional transesterification methods well known to practitioners of the organic chemical arts.

If, on the other hand, the desired end products of the reaction sequence are exclusively the substituted 5-oxo-2-pyrrolidinepropanoic acid esters, VIIIb, or the corresponding acids, VIIId, then a primary alcohol ester, such as the methyl, ethyl, or phenyl ester of the phosphorus ylid, IV, is employed in the first step of the reaction scheme (i.e., where $R_1$=methyl, ethyl, or phenyl).

The substituted cinnamic acid esters, V, are reacted with nitromethane in the presence of a base to produce the nitro-butyric acid esters, VI. This reaction introduces in the product molecules an asymmetric center at the carbon atom directly attached to the phenyl group. Condensation of the nitro-butyric acid esters, VI, with 1,1-dimethylethyl acrylate in the presence of a base introduces a second asymmetric center immediately adjacent to the first to yield VII, where $R_2$ is 1,1-dimethylethyl.

In the next step of the reaction sequence, the nitro-heptanedioic acid esters, VII, are reacted with hydrogen in the presence of a catalyst such as palladium/carbon to simultaneously reduce the nitro-group and, under these conditions, form the 5-oxo-pyrrolidine-ring to yield the esters VIIIa or VIIIb.

In this reaction, the resistance of the 1,1-dimethylethyl ester group at $R_1$ or $R_2$ to aminolysis causes the ring closure to be preferred through the aminolysis of the simple primary alcohol ester group. Thus, when $R_1$ is 1,1-dimethylethyl and $R_2$ is a simple group such as methyl, ethyl, or phenyl, ring closure results in the production of the substituted 5-oxo-2-pyrrolidine-propanoic esters, VIIIa. Contrariwise, when $R_2$ is 1,1-dimethylethyl and $R_1$ is a simple group such as methyl, ethyl, or phenyl, the reaction leads to the substituted 5-oxo-2-pyrrolidinepropanoic acid esters, VIIIb.

The esters, VIIIa and VIIIb are readily converted to the corresponding acids VIIIc and VIIId by hydrolysis. In those instances where $R_1$ and $R_2$ are phenyl or alkyl, such as methyl, ethyl, etc., basic hydrolysis of the esters, followed by acidification in dilute aqueous acid produces the corresponding acids. In those instances where $R_1$ and $R_2$ are 1,1-dimethylethyl, the acids are produced by acid catalyzed elimination of 2-methylene-propane from the esters, VIIIa and VIIIb in dilute aqueous acid.

The acids VIIIc and VIIId are convertible in hot acetic anhydride to the same bicyclic product, IX. Acid catalyzed hydrolysis of IX opens one ring or the other to produce a mixture of VIIIc and VIIId. Alternatively, acid catalyzed solvolysis of IX in alcohols produces a mixture of the esters, VIIIa and VIIIb.

Some examples of suitable pharmaceutical carriers, including pharmaceutical diluents, are sugars such as lactose and sucrose; starches such as corn starch and potato starch; cellulose derivatives such as sodium carboxymethylcellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol; glycerin; sorbitol; polyethylene glycol; water; agar; alginic acid; as well as other compatible substances normally employed in pharmaceutical formulations.

The pharmaceutical compositions of this invention can also contain other components such as coloring agents, flavoring agents, and/or preservatives. These latter materials, if present, are generally used in relatively small amounts. The compositions can, if desired, also contain other therapeutic agents, including other cognition activating agents such as 3-phenoxypyridine, and N-[N'N'-diisopropylaminoethyl]pyrrolidine-2-oxo-1-acetamide.

The percentage of active ingredient in the foregoing compositions can be varied within wide limits, but for practical purposes, the active ingredient is preferably present in a concentration of a least 10% in a solid composition, and at least 2% in a primarily liquid composition. The most satisfactory compositions are those in which a much higher proportion of the active ingredient is present. The pharmaceutical compositions of this invention contain from 0.1 to 250.0 mg, preferably from 1 to 25 mg of the active ingredient per dosage unit so that the entire amount to be administered during a day can be made from a reasonable number of dose units.

The compounds of the present invention may exist as solids in anhydrous form as well as forms which are solvated with water, alcohols, and other pharmaceutically acceptable solvents. These solid forms may be incorporated into formulations intended for parenteral administration. Such formulations may be either in solution form or in powdered form intended for combination with an isotonic solution containing other ingredients such as preservatives, etc.

The solid forms of the compounds of this invention may also be incorporated into suppository formulations intended for rectal administration or into syrup formulations intended for oral administration.

The mammalian dose range for a 70 kg subject is from 1 to 1500 mg of compound per day, preferably between about 25 mg to 750 mg per day, optionally administered in portions.

The compounds of the present invention are useful for treating senility or for reversing amnesia. The effectiveness of these compounds was evaluated by a test designed to show the ability of a given substance to reverse amnesia induced by electroconvulsive shock. The test is more fully described in U.S. Pat. No. 4,154,347, issued Mar. 20, 1979, and incorporated herein by reference. The only differences between the tests conducted in the present case and that described in the referenced patent were that in the present case, the test compounds were administered orally and the duration of the electrical shock used to induce amnesia in the test animals was 1.0 second.

The data from tests conducted employing compounds of the present invention appear in the Table I. The following criteria were used in interpreting the data: 40% or more amnesia reversal in the test animals=active, A; 25% to 39% amnesia reversal=borderline activity, C; 0% to 24% reversal of amnesia=inactive, N.

TABLE

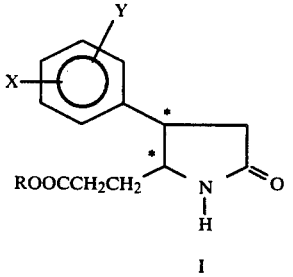

I

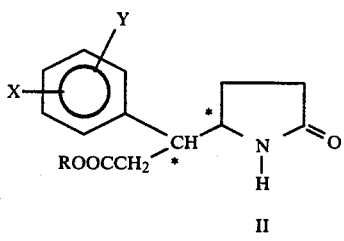

II

| Compound | X | Y | R | Activity 100 mg/kg | 10 mg/kg | 1 mg/kg |
|---|---|---|---|---|---|---|
| I & II (Mixture) | —H | —H | —CH$_2$—⌬ | 90(A) | 30(C) | 0(N) |

EXAMPLE 1

Preparation of 4-nitro-3-phenylheptanedioic acid dimethyl ester

A mixture of 300 g of cinnamic acid methyl ester, 500 g of nitromethane and 39 g of tetramethylguanidine is allowed to stir at room temperature for 72 hours. The solution is diluted with diethyl ether and aqueous hydrochloric acid solution (1 N, 1 liter) is added. The organic layer is separated, dried over anhydrous magnesium sulfate, and evaporated to give 4-nitro-3-phenylbutanoic acid methyl ester.

NMR (CDCl$_3$) δ=7.24 (s, 5H); 4.70 (d, J=14 Hz, 2H); 3.98 (m, J=14 Hz, 1H); 3.59 (s, 3H); 2.77 (d, J=14 Hz, 2H).

IR (cm$^{-1}$) 3030, 2960, 1735, 1600, 1550.

A solution of 356 g of 4-nitro-3-phenylbutanoic acid methyl ester, 138 g of methyl acrylate, and 25 ml of Triton B in 500 ml of t-butanol is allowed to stir at room temperature for 94 hours. Excess aqueous hydrochloric acid (1 N) is added and the solution is diluted with diethyl ether. The organic layer is separated, dried over anhydrous magnesium sulfate and evaporated to give 4-nitro-3-phenylheptanedioic acid dimethyl ester.

NMR (CDCl$_3$) δ=7.20 (m, 5H); 4.85 (m, 1H); 3.60 (s, 3H); 3.00-1.60 (m, 7H).

IR (cm$^{-1}$) 2960, 1740, 1552, 1440, 1367.

Preparation of, 5-oxo-3-phenyl-2-pyrrolidinepropanoic acid, 5-oxo-3-phenyl-2-pyrrolidinepropanoic acid methyl ester, 5-oxo-β-phenyl-2-pyrrolidinepropanoic acid, 5-oxo-β-phenyl-2-pyrrolidinepropanoic acid methyl ester A suspension of 120 g of 4-nitro-3-(phenyl)heptanedioic acid dimethyl ester and 5.5 g of 20% Pd/C in 1200 ml of methanol is placed under hydrogen atmosphere. After H$_2$ absorption is completed, the solution is filtered and the solvent is removed under reduced pressure to give a yellow oil that consists of a mixture of 5-oxo-3-phenyl-2-pyrrolidinepropanoic acid methyl ester, 5-oxo-β-phenyl-2-pyrrolidinepropanoic acid methyl ester and small amounts of the corresponding acids.

NMR (CDCl$_3$) δ=7.17 (s, 5H); 6.80 (s, 1H), 3.62 (m, 1H); 5.80 (s,3H); 3.20-1.72 (m, 7H).

IR (cm$^{-1}$) 3340, 3220, 3030, 2957, 1734, 1692, 1495, 1454, 1437.

A solution of 93.4 g of 5-oxo-3-phenyl-2-pyrrolidinepropanoic acid methyl ester and 5-oxo-β-phenyl-2-pyrrolidinepropanoic acid methyl ester in 370 ml of 1 N aqueous sodium hydroxide solution is heated to 60° C. for four hours. Excess aqueous hydrochloric acid (1 N, 380 ml) is added and the solution concentrated under reduced pressure to give 5-oxo-3-phenyl-2-pyrrolidinepropanoic acid and 5-oxo-β-phenyl-2-pyrrolidinepropanoic acid.

EXAMPLE 2

Preparation of 4-nitro-3-(4-methylphenyl)heptanedioic acid dimethyl ester

A suspension of 300 g of p-methylcinnamic acid (J. Chem. Soc., Chem. Comm., 471, 1976) and 25 ml of concentrated sulfuric acid in 1.7 liters of methanol is heated to reflux for 24 hours. The solution is concentrated, cooled and filtered to give as a white solid, p-methylcinnamic acid methyl ester, mp 55°-56° C. NMR (DMSOd$_6$) δ=7.36 (d, J=16 Hz, 1H); 7.36 (dd, J$_1$=30 Hz, J$_2$=7 Hz, 4H); 6.48 (d, J=16 Hz, 1H); 3.70 (s, 3H); 2.32 (s, 3H). IR (cm$^{-1}$) 3061, 3028, 2949, 1713, 1634, 1607, 1570, 1516, 1438.

A mixture to 300 g of p-methylcinnamic acid methyl ester, 500 g of nitromethane and 39 g of tetramethylguanidine is allowed to stir at room temperature for 72 hours. The solution is diluted with diethyl ether and (1 liter, 1 N) aqueous hydrochloric acid solution added. The organic layer is separated, dried over anhydrous magnesium sulfate, and evaporated to give 4-nitro-3-(4-methylphenyl) butanoic acid methyl ester.

NMR (CDCl$_3$) δ=7.10 (s, 4H); 4.63 (d, J=8 Hz, 2H); 3.91 (m, 1H); 3.56 (s, 3H); 2.78 (d, J=8 Hz, 2H); 2.25 (s, 3H).

IR (cm$^{-1}$) 2940, 1740, 1555, 1515, 1440, 1380, 1250, 1170.

A solution of 356 g of 4-nitro-3-(4-methylphenyl)butanoic acid methyl ester, 138 g of methyl acrylate and 25 ml of Triton B in 500 ml of t-butanol is allowed to stir at room temperature for 94 hours. Excess aqueous hydrochloric acid (1 N) is added and the solution is diluted with diethyl ether. The organic layer is separated, dried over anhydrous magnesium sulfate and evaporated to give 4-nitro-3-(4-methylphenyl)heptanedioic acid dimethyl ester.

NMR (CDCl$_3$) δ=7.13 (m, 4H); 4.83 (m, 1H); 3.66 (s, 3H); 3.60 (s, 3H); 3.10-1.77 (m, 10H).

IR (cm$^{-1}$) 2950, 1738, 1555, 1518, 1440, 1365, 1325, 1260.

Preparation of 3-(4-methylphenyl)-5-oxo-2-pyrrolidinepropanoic acid, 3-(4-methylphenyl)-5-oxo-2-pyrrolidinepropanoic acid methyl ester, β-(4-methylphenyl)-5-oxo-2-pyrrolidinepropanoic acid, β-(4-methylphenyl)-5-oxo-2-pyrrolidinepropanoic acid methyl ester A suspension of 120 g of 4-nitro-3-(4-methylphenyl)-heptanedioic acid dimethyl ester and 5.5 g of 20% Pd/C in 1200 ml of methanol is placed under hydrogen atmosphere. After H₂ absorption is completed, the solution is filtered and the solvent is removed under reduced pressure to give a yellow oil that consists of a mixture of 3-(4-methylphenyl)-5-oxo-2-pyrrolidinepropanoic acid methyl ester, β-(4-methylphenyl)-5-oxo-2-pyrrolidinepropanoic acid methyl ester, and small amounts of the corresponding acids.

NMR (CDCl₃) δ=7.50 (s, 4H); 7.21 (s, 1H); 4.02 (m, 1H); 3.32–1.75 (m, 10H). IR (cm⁻¹) 3190, 3000, 2925, 1730, 1685, 1540, 1490, 1450, 1435, 1360.

A solution of 93.4 g of 3-(4-methylphenyl)-5-oxo 2-pyrrolidinepropanoic acid methyl ester and β-(4-methylphenyl)-5-oxo-2-pyrrolidinepropanoic acid methyl ester in 370 ml of 1 N aqueous sodium hydroxide solution is heated to 60° C. for four hours. Excess aqueous hydrochloric acid (1 N, 380 ml) is added and the solution is concentrated under reduced pressure to give β-(4-methylphenyl)-5-oxo-2-pyrrolidinepropanoic acid and 3-(4-methylphenyl)-5-oxo-2-pyrrolidinepropanoic acid.

EXAMPLE 3

Preparation of 4-nitro-3-(4-chlorophenyl)heptanedioic acid dimethyl ester

A suspension of 300 g of 4-chlorocinnamic acid (*J. Am. Chem. Soc.*, 89:3803, 1967) and 25 ml of concentrated sulfuric acid in 1.7 liters of methanol is heated to reflux for 24 hours. The solution is concentrated, and filtered to give as a white solid, p-chlorocinnamic acid methyl ester, mp 74°–5° C.

NMR (CDCl₃) δ=7.65 (d, J=16 Hz, 1H); 7.37 (m, 4H); 6.40 (d, J=16 Hz, 1H); 3.81 (s, 3H).

IR (cm⁻¹) 3036, 2952, 1710, 1670, 1635, 1593.

A mixture of 290 g of p-chlorocinnamic acid methyl ester, 500 g of nitromethane and 39 g of tetramethylguanidine is allowed to stir for 72 hours. The solution is diluted with ethyl ether and aqueous hydrochloric acid solution (1 N, 1 liter) is added. The organic layer is separated, dried over anhydrous magnesium sulfate, and evaporated to give 4-nitro-3-(4-chlorophenyl)butanoic acid methyl ester.

NMR (CDCl₃) δ=7.23 (m, 4H); 4.73 (d, J=8 Hz, 2H); 4.10 (m, 1H); 3.65 (s, 3H); 2.75 (d, J=8 Hz, 2H).

IR (cm⁻¹) 2930, 1735, 1590, 1550, 1490, 1435, 1375, 1320.

A solution of 337 g of 4-nitro-3-(4-chlorophenyl)-butanoic acid methyl ester, 118 g of methyl acrylate, and 25 ml of Triton B in 500 ml of t-butanol is allowed to stir at room temperature for 94 hours. Excess aqueous hydrochloric acid (1 N) is added and the solution is diluted with diethyl ether. The organic layer is separated, dried over anhydrous magnesium sulfate and evaporated to give 4-nitro-3-(4-chlorophenyl)heptanedioic acid dimethyl ester.

NMR (CDCl₃) δ=7.23 (m, 4H); 4.73 (m, 1H); 3.60 (s, 3H); 3.47 (s, 3H); 2.93–1.64 (m, 7H).

IR (cm⁻¹) 2940, 1740, 1555, 1470, 1440, 1365, 1250.

Preparation of
3-(4-chlorophenyl)-5-oxo-2-pyrrolidinepropanoic acid,
3-(4-chlorophenyl)-5-oxo-2-pyrrolidinepropanoic acid methyl ester,
β-(4-chlorophenyl)-5-oxo-2-pyrrolidinepropanoic acid,
β-(4-chlorophenyl)-5-oxo-2-pyrrolidinepropanoic acid methyl ester A suspension of 51.5 g 4-nitro-3-(4-chlorophenyl)heptanedioic acid dimethyl ester, 52 g of iron powder and 7 ml of concentrated hydrochloric acid in 500 ml ethanol/water (1:1) is heated to reflux for 14 hours. After filtering off the insolubles and evaporation of solvent, the resulting oil is chromatographed over silica gel (mesh size 200–400) (elution with chloroform) to give a mixture consisting of 3-(4-chlorophenyl)-5-oxo-2-pyrrolidinepropanoic acid methyl ester and β-(4-chlorophenyl)-5-oxo-2-pyrrolidinepropanoic acid methyl ester.

NMR (CDCl₃) δ=8.05 (s, 1H); 7.34 (m, 4H); 4.08 (m, 1H); 3.52 (s, 3H); 3.32–1.00 (m, 7H).

IR (cm⁻¹) 3200, 3050, 2930, 1725, 1680, 1585, 1430.

A solution of 36.7 g of 3-(4-chlorophenyl)-5-oxo-2-pyrrolidinepropanoic acid methyl ester and β-(4-chlorophenyl)-5-oxo-2-pyrrolidinepropanoic acid methyl ester in aqueous sodium hydroxide (1 N, 130 ml) solution is heated to 60° C. for four hours. Excess aqueous hydrochloric acid (1 N, 140 ml) is added and solution is concentrated under reduced pressure to give β-(4-chlorophenyl)-5-oxo-2-pyrrolidinepropanoic acid and 3-(4-chlorophenyl)-5-oxo-2-pyrrolidinepropanoic acid.

EXAMPLE 4

Preparation of
4-nitro-3-(3,4-dichlorophenyl)heptanedioic acid dimethyl ester

A suspension of 300 g of 3,4-dichlorocinnamic acid (*J. Org. Chem.*, 26:2991 (1961)) and 25 ml of concentrated sulfuric acid in 1.7 liters of methanol is heated to reflux for 24 hours. The solution is concentrated, cooled, and filtered to give as a white solid, 3,4-dichlorocinnamic acid methyl ester, mp 114°–15° C.

NMR (CDCl₃) δ=7.40 (m, 4H); 6.33 (d, J=16 Hz, 1H); 3.72 (s, 3H).

IR (cm⁻¹) 3093, 3035, 1719, 1643, 1483, 1434, 1322, 1213.

A mixture of 300 g of 3,4-dichlorocinnamic acid methyl ester, 400 g of nitromethane and 26 g of tetramethylguanidine is allowed to stir for 72 hours. The solution is diluted with ethyl ether and aqueous hydrochloric acid solution (1 N, 1 liter) is added. The organic layer is separated, dried over anhydrous magnesium sulfate, and evaporated to give 4-nitro-3-(3,4-dichlorophenyl)butanoic acid methyl ester.

NMR (CDCl₃) δ=7.27 (m, 3H); 4.70 (d, J=8 Hz, 2H); 4.00 (m, 1H); 3.62 (s, 3H); 2.76 (d, J=8 Hz, 2H).

IR (cm⁻¹) 2950, 2880, 1725, 1549, 1410, 1265, 1090, 1015, 800.

A solution of 350 g of 4-nitro-3-(3,4-dichlorophenyl)-butanoic acid methyl ester, 118 g of methyl acrylate and 25 ml of Triton B in 500 ml of t-butanol is allowed to stir at room temperature for 94 hours. Excess aqueous hydrochloric acid (1 N) is added and the solution is diluted with diethyl ether. The organic layer is separated, dried over anhydrous magnesium sulfate and evaporated to give 4-nitro-3-(3,4-dichlorophenyl)heptanedioic acid dimethyl ester.

NMR (CDCl₃) δ=7.20 (m, 3H); 4.84 (m, 1H); 4.10 (m, 1H); 3.60 (s, 3H); 3.50 (s, 3H); 3.17–1.67 (m, 6H).

IR (cm⁻¹) 2970, 1725, 1555, 1495, 1440, 1420, 1375.

Preparation of
3-(3,4-dichlorophenyl)-5-oxo-2-pyrrolidinepropanoic acid,
3-(3,4-dichlorophenyl)-5-oxo-2-pyrrolidinepropanoic acid methyl ester,
β-(3,4-dichlorophenyl)-5-oxo-2-pyrrolidinepropanoic acid,
β-(3,4-dichlorophenyl)-5-oxo-2-pyrrolidinepropanoic acid methyl ester A suspension of 56.6 g 4-nitro-(3-4-dichlorophenyl)-heptanedioic acid dimethyl ester, 60 g of iron powder and 7 ml of concentrated hydrochloric acid in 500 ml ethanol/water (1:1) is heated to reflux for 14 hours. After filtering off the insolubles and evaporation of the solvent, the resulting oil is chromagraphed over silica gel (mesh size 200-400) (elution with chloroform) to give a mixture that consists of 3-(3,4-dichlorophenyl)-5-oxo-2-pyrrolidinepropanoic acid methyl ester and β-(3,4-dichlorophenyl)-5-oxo-2-pyrrolidinepropanoic acid methyl ester.

NNR (CDCl$_3$) δ=7.51 (s, 1H); 7.11 (m, 3H); 4.14 (m, 1H); 3.62 (s, 3H); 3.05-1.72 (m, 7H).

IR (cm$^{-1}$) 3175, 3070, 2925, 1725, 1690, 1580, 1540, 1465, 1430.

A solution of 34.1 g of 3-(3,4-dichlorophenyl)-5-oxo-2-pyrrolidinepropanoic acid methyl ester and β-(3,4-dichlorophenyl)-5-oxo-2-pyrrolidinepropanoic acid methyl ester in aqueous sodium hydroxide solution (1 N, 108 ml) is heated to 60° C. for four hours. Excess aqueous hydrochloric acid (1 N, 120 ml) is added and the solution is concentrated under reduced pressure to give β-(3,4-dichlorophenyl)-5-oxo-2-pyrrolidinepropanoic acid and 3-(3,4-dichlorophenyl)-5-oxo-2-pyrrolidinepropanoic acid.

EXAMPLE 5

Preparation of
4-nitro-3-(4-trifluoromethylphenyl)heptanedioic acid ethyl, methyl ester A suspension of 300 g of 4-trifluoromethylcinnamic acid (*J. Org. Chem.* 43:980 (1978)) and 25 ml of concentrated sulfuric acid in 1.7 liters of ethanol is heated to reflux for 24 hours. The solution is concentrated, cooled, and filtered to give as a white solid, 4-trifluoromethylcinnamic acid ethyl ester, mp 40°-41° C.

NMR (CDCl$_3$) δ=7.83 (m, 4H); 7.68 (d, J=15 Hz, 1H); 6.75 (d, J=15 Hz, 1H); 4.19 (q, J=6 Hz, 2H); 1.20 (t, J=6 Hz, 3H).

IR (cm$^{-1}$) 2980, 1715, 1644, 1479, 1442, 1368, 1336.

A mixture of 300 g of 4-trifluoromethylcinnamic acid ethyl ester, 500 g of nitromethane, and 39 g of tetramethylguanidine is allowed to stir for 72 hours. The solution is diluted with diethyl ether and aqueous hydrochloric acid solution (1 N, 1 liter) is added. The organic layer is separated, dried over anhydrous magnesium sulfate and evaporated to give 4-nitro-3-(4-trifluoromethylphenyl)butanoic acid ethyl ester.

NMR (CDCl$_3$) δ=7.54 (s, 4H); 4.76 (d, J=18 Hz, 2H); 4.15 (m, 1H); 4.10 (q, J=7 Hz, 2H); 2.80 (d, J=8 Hz, 2H); 1.17 (t, J=7 Hz, 3H).

IR (CM$^{-1}$) 2970, 1735, 1555, 1455, 1380, 1330.

A solution of 356 g of 4-nitro-3-(4-trifluoromethylphenyl)butanoic acid ethyl ester, 138 g of methyl acrylate, and 25 ml of Triton B in 500 ml of butanol is allowed to stir at room temperature for 94 hours. Excess aqueous hydrochloric acid (1 N), is added and the solution is diluted with diethyl ether. The organic layer is separated, dried over anhydrous magnesium sulfate and evaporated to give 4-nitro-3-(4-trifluoromethylphenyl)-heptanedioic acid ethyl, methyl ester.

NMR (CDCl$_3$) δ=7.44 (s, 4H); 4.82 (m, 1H); 3.65 (s, 3H); 3.58 (s, 3H); 3.22-1.70 (m, 7H).

IR (cm$^{-1}$) 2910, 2840, 1740, 1540, 1460, 1375.

Preparation of
5-oxo-3-[4-(trifluoromethyl)phenyl]-2-pyrrolidinepropanoic acid,
5-oxo-3-[4-(trifluoromethyl)phenyl]-2-pyrrolidinepropanoic acid methyl ester,
5-oxo-β-[4-(trifluoromethyl)phenyl]-2-pyrrolidinepropanoic acid,
5-oxo-β-[4-(trifluoromethyl)phenyl]-2-pyrrolidinepropanoic acid ethyl ester A suspension of 120 g of 4-nitro-3-(4-trifluoromethylphenyl)heptanedioic acid ethyl, methyl ester and 5.5 g of 20% Pd/C in 1200 ml of methanol is placed under hydrogen atmosphere. After H$_2$ absorption is complete, the solution is filtered and the methanol removed under reduced pressure to give a yellow oil that consists of a mixture of 5-oxo-3-[4-(trifluoro-methyl)phenyl]-2-pyrrolidinepropanoic acid methyl ester and ester and 5-oxo-β-[4-(trifluoromethyl)phenyl]-2-pyrrolidinepropanoic acid ethyl ester, and small amounts of the corresponding acids. NMR (CDCl$_3$) δ=8.35 (s, 1H); 7.53 (s, 4H); 4.15 (m, 3H); 3.60-1.75 (m, 7H); 1.20 (m, 3H). IR (cm$^{-1}$) 3200, 3010, 1725, 1690, 1540, 1450, 1380, 1330.

A solution of 93.4 g of 5-oxo-3-[4-(trifluoromethyl)phenyl]-2-pyrrolidinepropanoic acid methyl ester and 5-oxo-β-[4-(trifluoromethyl)phenyl]-2-pyrrolidinepropanoic acid ethyl ester in aqueous sodium hydroxide solution (1 N, 370 ml) is heated to 60° C. for four hours. Excess aqueous hydrochloric acid (1 N, 370 ml) is added and the solution is concentrated under reduced pressure to give 5-oxo-β-[4-(trifluoromethyl)phenyl]-2-pyrrolidinepropanoic acid and 5-oxo-3-[4-(trifluoromethyl)phenyl]-2-pyrrolidinepropanoic acid.

EXAMPLE 6

Preparation of
4-nitro-3-(4-methoxyphenyl)heptanedioic acid dimethyl ester

A suspension of 300 g of 4-methoxycinnamic acid (*J. Chem. Soc., Chem. Comm.*, 355, (1978)) and 25 ml of concentrated sulfuric acid in 1.7 liters of methanol is heated to reflux for 96 hours. The solution is concentrated, cooled, and filtered to give as a white solid, 4-methoxycinnamic acid methyl ester, mp 85°-86° C.

NMR (DMSOd$_6$) δ=7.53 (d, J=15 Hz, 1H); 7.48 (d, J=9 Hz, 2H); 6.88 (d, J=9 Hz, 2H), 6.38 (d, J=15 Hz, 1H); 3.75 (s, 3H); 3.67 (s, 3H).

IR (cm$^{-1}$) 2951, 2845, 1715, 1638, 1605, 1577, 1514.

A mixture of 288 g of 4-methoxycinnamic acid methyl ester, 500 g of nitromethane and 23 g of tetramethylguanidine is allowed to stir for 72 hours. The solution is diluted with diethyl ether and aqueous hydrochloric acid solution (1 N, 1 liter) is added. The organic layer is separated, dried over anhydrous magnesium sulfate, and evaporated to give 4-nitro-3-(4-methoxyphenyl)butanoic acid methyl ester.

NMR (CDCl$_3$) δ=6.89 (m, 4H), 4.00 (d, J=14 Hz, 2H); 3.84 (m, 1H); 3.63 (s, 3H); 3.42 (s, 3H); 2.60 (d, J=14 Hz, 2H).

IR (cm$^{-1}$) 3004, 2954, 2840, 1737, 1635, 1605, 1585, 1577, 1554.

A solution of 200 g of 4-nitro-3-(4-methoxyphenyl)-butanoic acid methyl ester, 68 g of methyl acrylate, and 25 ml of Triton B in 500 ml of t-butanol is allowed to stir at room temperature for 94 hours. Excess aqueous hydrochloric acid (1 N) is added and the solution is diluted with diethyl ether. The organic layer is separated, dried over anhydrous magnesium sulfate, and evaporated to give 4-nitro-3-(4-methoxyphenyl)heptanedioic acid dimethyl ester.

NMR (CDCl$_3$) δ=6.90 (m, 4H); 3.78–3.27 (m, 10H); 2.90–1.77 (m, 7H).

IR (cm$^{-1}$) 2975, 2930, 2810, 1730, 1630, 1600, 1550, 1510, 1480, 1440, 1380.

Preparation of
3-(4-methoxyphenyl)-5-oxo-2-pyrrolidinepropanoic acid,
3-(4-methoxyphenyl)-5-oxo-2-pyrrolidinepropanoic acid methyl ester,
β-(4-methoxyphenyl)-5-oxo-2-pyrrolidinepropanoic acid,
β-(4-methoxyphenyl)-5-oxo-2-pyrrolidinepropanoic acid methyl ester A suspension of 120 g of 4-nitro-3-(4-methoxyphenyl)heptanedioic acid dimethyl ester and 5.5 g of 20% Pd/C in 120 ml of methanol is placed under hydrogen atmosphere. After H$_2$ absorption is complete, the solution is filtered and the solvent removed under reduced pressure to give a yellow oil that consists of a mixture of 3-(4-methoxyphenyl)-5-oxo-2-pyrrolidinepropanoic acid methyl ester and β-(4-methoxyphenyl)-5-oxo-2-pyrrolidinepropanoic acid methyl ester and small amounts of the corresponding acids.

NMR (CDCl$_3$) δ=7.87 (s, 1H); 6.90 (m, 4H); 3.77 (s, 3H); 3.67 (s, 3H); 3.50 (m, 1H); 3.10–1.60 (m, 7H).

IR (cm$^{-1}$) 3630, 3560, 2990, 1725, 1690, 1600, 1505, 1430.

EXAMPLE 7

Preparation of
trans-dihydro-1-phenyl-1H̄-pyrrolizine-3,5(2H̄,6H̄)-dione and
cis-dihydro-1-phenyl-1H̄-pyrrolizine-3,5(2H̄,6H̄)-dione
(as a mixture)

A solution of 93.4 g of 5-oxo-3-phenyl-2-pyrrolidinepropanoic acid methyl ester and 5-oxo-βphenyl-2-pyrrolidinepropanoic acid methyl ester in 370 ml of 1N aqueous sodium hydroxide solution is heated to 60° C. for four hours. Excess aqueous hydrochloric acid (1 N, 370 ml) is added and the solution is concentrated under reduced pressure to yield 5-oxo-β-phenyl-2-pyrrolidinepropanoic acid and 5-oxo-3-phenyl-2-pyrrolidinepropanoic acid. The acids are dissolved in 300 ml of acetic anyhydride and the solution heated to 90° C. The solution is filtered hot and the filtrate concentrated in vacuo. The oil is chromatographed on silica gel (200–400 mesh) to give cis- and trans-dihydro-1-phenyl-1H̄-pyrrolizine-3,5(2H̄,6H̄)-diones as a white solid with mp 151°–3° C.

NMR (CDCl$_3$) δ=7.39 (m, 5H); 4.71(dt, J$_1$=7 Hz, J$_2$=10 Hz, 1H); 4.46 (dt, J$_1$=10 Hz, J$_2$=6 Hz, 1H); 3.84–1.15 (m, 7H).

IR (cm$^{-1}$) 3025, 2990, 1775, 1695, 1603, 1500.

Preparation of 5-oxo-4-phenyl-2-pyrrolidinepropanoic acid phenylmethyl ester and
5-oxo-β-phenyl-2-pyrrolidinepropanoic acid phenylmethyl ester A solution of 4.3 g of cis- and trans-dihydro-1-phenyl-1H̄-pyrrolizine-3,5(2H̄,6H̄)-dione in 50 ml of phenylmethanol is treated with three drops of concentrated sulfuric acid and the resulting mixture is heated at 90° C. for 36 hours.

Thin-layer chromatography on silica plates (developed with dichloromethane) demonstrates the absence of the starting dione at this point. The greater portion of the excess phenylmethanol is removed by distillation at 0.1 mm Hg.

The resulting oil is chromatographed over silica, eluting with 2-propanol:dichloromethane, 5:95. The product (mixture of esters) is isolated by concentration, mp 141°–148° C.

NMR (CHCl$_3$)=7.33 (m, 10H), 6.83 (s, 2H), 3.82 (m, 2H), 2.83–1.29 (m, 6H).

IR (cm$^{-1}$) 3455, 3225, 2930, 1737, 1696, 1662, 1450, 1355, 1215.

We claim:

1. A compound having structural formula I

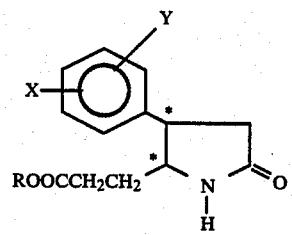

wherein R is hydrogen, or a pharmaceutically acceptable cation, alkyl of from one to six carbon atoms, or phenylmethyl, and X and Y are independently hydrogen, alkyl of from one to six carbon stoms, alkoxy of from one to six carbon atoms, chloro-, or trifluoromethyl.

2. A compound in accordance with claim 1 wherein R is hydrogen, or a pharmaceutically acceptable cation.

3. A compound in accordance with claim 1 wherein R is alkyl of from one to six carbon atoms, or phenylmethyl.

4. A compound in accordance with claim 2 and being 5-oxo-3-phenyl-2-pyrrolidinepropanoic acid or a pharmaceutically acceptable acid addition salt thereof.

5. A compound in accordance with claim 2 and being 3-(4-methylphenyl)-5-oxo-2-pyrrolidinepropanoic acid or a pharmaceutically acceptable acid addition salt thereof.

6. A compound in accordance with claim 2 and being 3-(4-chlorophenyl)-5-oxo-2-pyrrolidinepropanoic acid or a pharmaceutically acceptable acid addition salt thereof.

7. A compound in accordance with claim 2 and being 3-(3,4-dichlorophenyl)-5-oxo-2-pyrrolidinepropanoic acid or a pharmaceutically acceptable acid addition salt thereof.

8. A compound in accordance with claim 2 and being 3-(4-(trifluoromethyl)phenyl)-5-oxo-2-pyrrolidinepropanoic acid or a pharmaceutically acceptable acid addition salt thereof.

9. A compound in accordance with claim 2 and being 3-(4-methoxyphenyl)-5-oxo-2-pyrrolidinepropanoic acid or a pharmaceutically acceptable acid addition salt thereof.

10. A compound in accordance with claim 3 and being 5-oxo-3-phenyl-2-pyrrolidinepropanoic acid methyl ester.

11. A compound in accordance with claim 3 and being 3-(4-methylphenyl)-5-oxo-2-pyrrolidinepropanoic acid methyl ester.

12. A compound in accordance with claim 3 and being 5-oxo-3-phenyl-2-pyrrolidinepropanoic acid phenylmethyl ester.

13. A compound in accordance with claim 3 and being 3-(4-chlorophenyl)-5-oxo-2-pyrrolidinepropanoic acid methyl ester.

14. A compound in accordance with claim 3 and being 3-(3,4-dichlorophenyl)-5-oxo-2-pyrrolidinepropanoic acid methyl ester.

15. A compound in accordance with claim 3 and being 5-oxo-3-[4-trifluoromethyl)phenyl]-2-pyrrolidinepropanoic acid methyl ester.

16. A compound in accordance with claim 3 and being 3-(4-methoxyphenyl)-5-oxo-2-pyrrolidinepropanoic acid methyl ester.

17. A compound in accordance with claim 3 and being 3-[4-trifluoromethyl)phenyl]-5-oxo-2-pyrrolidinepropanoic acid ethyl ester.

18. A pharmaceutical composition for reversing electroconvulsive shock-induced amnesia comprising an effective amount of a compound in accordance with claim 1 in combination with a pharmaceutically acceptable carrier.

19. A method of reversing electroconvulsive shock-induced amnesia comprising administering to a mammal in need of such treatment an effective amount of a pharmaceutical composition in accordance with claim 18.

* * * * *